United States Patent [19]

Fujii et al.

[11] Patent Number: 4,772,553
[45] Date of Patent: Sep. 20, 1988

[54] METHOD FOR DETERMINATION OF ENZYME ACTIVITY

[75] Inventors: Setsuro Fujii, Toyonaka; Satoshi Sugiyama; Syouzou Sawai, both of Chiba, all of Japan

[73] Assignee: Torii & Co., Inc., Tokyo, Japan

[21] Appl. No.: 875,161

[22] Filed: Jun. 17, 1986

Related U.S. Application Data

[63] Continuation-in-part of Ser. No. 517,314, Jul. 26, 1983, abandoned.

[30] Foreign Application Priority Data

Aug. 3, 1982 [JP] Japan ................. 57-135534

[51] Int. Cl.$^4$ .......... C12Q 1/56; C12Q 1/44; C12Q 1/38; C12N 9/99
[52] U.S. Cl. ................. 435/13; 435/19; 435/23; 435/184
[58] Field of Search .......... 435/13, 23, 24, 29, 435/34, 39, 184, 19; 436/903

[56] References Cited

U.S. PATENT DOCUMENTS

| | | | |
|---|---|---|---|
| 3,862,011 | 1/1975 | Smith | 435/24 |
| 4,257,940 | 3/1981 | Fujii et al. | 435/4 |
| 4,308,201 | 12/1981 | Fujii | 435/13 |
| 4,308,202 | 12/1981 | Fijii et al. | 435/13 |

FOREIGN PATENT DOCUMENTS

WO8000351  3/1980  PCT Int'l. Appl. .................. 435/24

OTHER PUBLICATIONS

Sanders et al., Clin. Chim. Acta, 89: 421–427, "Interference with the Kinetic Determination of Acid Phosphatase", (1978).

Thielemann, Chemical Abstracts, 81:72336j, p. 627 (1974).

Holzmann et al, J. Immunol. Meth. 60:359–367, Jun. 10, 1983.

Primary Examiner—Esther M. Kepplinger
Attorney, Agent, or Firm—Beveridge, DeGrandi & Weilacher

[57] ABSTRACT

This invention relates to a method for determining an enzyme-, an enzyme inhibitor-, an enzyme activator-, or zymogen-activity, which comprises allowing the enzyme to react with a substrate of the formula

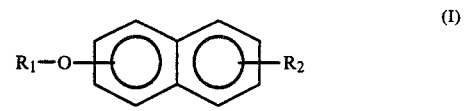

(I)

(wherein $R_1$ represents an amino acid of an oligopeptide combined in the form of ester through the C-terminal carboxyl group of said amino acid or oligopeptide and $R_2$ represents a hydrogen or bromine atom) to hydrolyze the substrate, then allowing the hydrolysis product of the formula

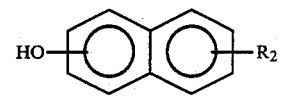

to react with a FR-ITR salt [Fast Red-ITR salt (N,N'-diethyl-4-methoxymetanilamide diazonium salt)] to form a pigment, and determining the pigment.

21 Claims, 6 Drawing Sheets

METHOD FOR DETERMINATION OF ENZYME ACTIVITY

CROSS REFERENCE TO RELATED APPLICATION

This application is a continuation-in-part of application Ser. No. 517,314, filed July 26, 1983, now abandoned, the entire disclosure of which is relied upon and incorporated herein by reference.

This invention relates to a method for determining an enzyme-, an enzyme inhibitor-, an enzyme activator-, or zymogen-activity, which comprises allowing the enzyme to react with a substrate of the formula (wherein $R_1$ represents an amino acid or an oligopeptide combined in the form of ester through the C-terminal carboxyl group of said amino acid or oligopeptide and $R_2$ represents a hydrogen or bromine atom) to hydrolyze the substrate, then allowing the hydrolysis product of the formula to react with a FR-ITR salt [Fast Red-ITR salt (N,N'-diethyl-4-methoxymetanilamide diazonium salt)] to form a pigment, and determining the pigment.

The enzyme, as herein referred to, is that which is able to hydrolyze the compound of formula (I). Such enzymes include serine proteases such as trypsin, chymotrypsin, kallikrein, plasmin, thrombin, urokinase, factor Xa, $\overline{Cls}$ and $\overline{Clr}$, other proteases and esterases, and unknown enzymes capable of hydrolyzing the compounds of formula (I). As examples of the assay of unknown enzymes by the method of this invention, mention may be made of the electrophoretic determination of enzyme pattern of the blood or urine and the cell staining.

The present method is effectively applicable to the assay of serine protease of E.C. 3.4.21 among various enzymes. Among the serine proteases, those which are especially effectively assayed by the present method are trypsin, chymotrypsin, kallikrein, plasmin, thrombin, urokinase, factor Xa, $\overline{Cls}$ and $\overline{Clr}$. It is also possible to apply the present method to the assay of inhibitors, activators, and zymogens for the above enzymes, such as, for example, antithrombin III, heparin, $\alpha_2$-plasmin-inhibitor, $\alpha_1$-trypsin-inhibitor, streptokinase, Echis carinatus venom (ECV), prekallikrein, plasminogen and prothrombin.

In the formula (I), $R_1$ represents an amino acid or an oligopeptide which is combined in the form of ester through the C-terminal carboxyl group of said amino acid or oligopeptide. The term "an amino acid or an oligopeptide" as herein used, means any simple amino acid or an oligopeptide comprising 2 to 4 amino acid which may be each the same or different, the N-terminal remaining free or bearing an acyl or sulfonyl group. As examples of amino acids, mention may be made of L, D, and DL forms of Gly, Ala, Val, Leu, Ile, Met, Pro, Phe, Gln, Glu, pyroGlu, Lys, Lys(Me), Arg, and Tyr.

As examples of suitable substrates of formula (I), mention may be made of those in which $R_1$ is A-$R_3$-$R_4$-$R_5$-$R_6$-CO-, wherein A represents a hydrogen atom or an acyl or sulfonyl group, $R_3$ to $R_5$ represent each Gly, Ala, Val, Leu, Ile, Pro, Phe, Gln, Glu, pyroGlu, or a single bond, and $R_6$ represents Lys, Lys(Me), Arg, Met, or Tyr. Preferred examples of A include hydrogen atom, Ac, Bz, Tos, Boc, Cbz, dansyl, and Glt. Examples of preferred substrates are those in which $R_1$ is A-Tyr-, A-Arg-, A-Lys-, A-Gly-Lys-, A-Phe-Arg-, A-Gly-Gly-Arg-, A-Leu-Gly-Arg-, A-Gln-Gly-Arg-, A-pyroGlu-Gly-Arg-, A-Leu-Ala-Arg-, A-Pro-Phe-Arg-, A-Val-Leu-Lys-, A-Phe-Val-Arg-, or A-Ile-Glu-Gly-Arg-. Examples of most preferred substrates are those of the formula (I) of Tos-Lys-$\alpha$-NE, Ac-Tyr-$\alpha$-NE, Bz-Leu-Ala-Arg-$\alpha$-NE, Ac-Phe-Arg-$\alpha$-NE, H-Pro-Phe-Arg-$\alpha$-NE, and Ac-Gly-Lys-$\alpha$-NE.

In the formula (I) $R_2$ is a hydrogen or bromine atom. As examples of bromo derivatives, mention may be made of those in which bromine is attached at position 6. Thus, the compound of formula (I) according to this invention is a compound in which the C-terminal of the above-mentioned amino acids or oligopeptides is combined with the compound of the formula through an ester linkage.

Although the time and temperature of the reaction between the enzyme and the substrate depend upon the reactivities and quantities of both reactants, the reaction time is generally 2 hours or less, preferably from 30 seconds to 90 minutes and the reaction temperature is generally from 20° to 40° C., preferably from 20° to 37° C. The FR-ITR salt [Fast RedITR salt (N,N'-diethyl-4-methoxymetanilamide diazonium salt)] has the formula (where X represents a halogen atom), preferably in the form of an addition product with $\frac{1}{2}$ $ZnCl_2$.

The pigment formed by the reaction between FR-ITR salt and the compound which is produced by the hydrolysis of the substrate [formula (I)] with an enzyme, is an azo pigment. The reaction time of this color reaction is 2 hours or less, possibly from 30 seconds to 90 minutes. The reaction between a substrate and an enzyme and the color reaction with the FR-ITR salt may be carried out either successively or simultaneously. The amount of pigment which is formed is measured spectroscopically using a colorimeter or a spectrophotometer or visually. The wave length employed in the spectroscopic measurement is 450 to 550 nm in most cases. The visual estimation is employed in the determination by comparison with a standard, in the electrophoretic determination of an enzyme pattern, or in the cell staining.

The assay of an enzyme activity is important in the quality control of enzyme preparations, in clinic examination, and in the diagnosis of various diseases by examining the enzyme content of the blood or urine.

Various methods have been known for the assay of enzyme activity. The method using a synthetic substrate is one of the most frequently employed methods. Among the synthetic substrates, a naphthol ester of an amino acid or a peptide is known to be an excellent substrate [Japanese Patent Application "Kokai" (Laid-open) Nos. 63,049/79 and 59,151/80; hereinafter to as disclosed method]. According to the disclosed method, in which the enzyme activity is assayed by use of such a naphthol ester, the naphthol liberated by hydrolysis with an enzyme is allowed to react with FVB salt [Fast Violet B salt (6-benzamido-4-methoxy-m-toluidine diazonium salt)] to yield an azo pigment which is then determined. In the disclosed method, the reaction between the liberated naphthol and the FVB salt is carried out while cooling in ice-water, because otherwise the hydrolysis of the diazonium reagent itself or an interreaction of the diazonium reagent will take place, resulting in fluctuation of the observed absorbance or $\lambda_{max}$. As contrasted, in the method of this invention, the reaction between the liberated compound and the FR-ITR salt is carried out in the temperature range of from 0° C. to 40° C., without causing fluctuation of the observed absorbance or $\lambda_{max}$, as described later in Example 1. In the disclosed method, the reaction time of the reaction between the liberated naphthol and the FVB salt must be rigidly controlled, because the absorbance varies with the reaction time. To the contrary, in the method of the present invention, the reaction between the liberated compound and the FR-ITR salt becomes rapidly complete and the absorbance remains unchanged even after completion of the reaction.

As stated above, in the disclosed method it is necessary to change the temperature conditions of the reaction system from those (generally 20° to 40° C.) in the step of reaction between the enzyme and the substrate to those (0° C. or thereabout) in the step of color reaction and, moreover, to perform the absorbance measurement in accordance with the prescribed time schedule. Therefore, it is an important advantage of the method of this invention that it is no longer necessary to maintain different temperatures in both steps and to set a precise time limit in the color reaction step. This is of important significance, because the present invention not only simplifies the assay procedure but also renders it possible to adapt the assay procedure to an autoanalyzer wherein it is difficult to change the operation temperature.

Another disadvantage of the disclosed method is the fluctuation of observed values which frequently occurs in the assay of enzyme activity in urine. Such fluctuation was found to be caused by the presence of nitrite ion, which is unavoidable when a microorganism contaminated the urine. The presence of nitrite ion in urine, which is independent of the enzymes in urine, has been an obstacle to the application of the disclosed method to the assay of enzymes in urine [Nippon Rinsho (Japan Clinic), Vol. 37, Special number for the Summer, 2668 (1979)]. The method of this invention has an advantage of being not susceptible to the adverse effect of the nitrite ion, as described later in Example 2.

In practice, it frequently occurs to terminate the reaction between enzyme and substrate by acidifying the reaction mixture before being subjected to the color reaction. In the disclosed method employing the FVB salt, however, the color reaction does not proceed in an acidic region (pH 1-4), whereas in the method of this invention, coloration takes place even in such an acidic region. It is, therefore, another advantage of the present method that after the reaction between enzyme and substrate has been terminated by acidification, the reaction mixture can be directly subjected to the color reaction.

Another advantage of this invention is that the coupling reaction between the hydrolysis product and the FR-ITR salt yields more accurate and reproducible results when carried out in the dark than the disclosed method. In addition, the method of this invention yields more accurate and reproducible absorbance measurements than the disclosed method when the coupling reaction is carried out in outdoor or indoor light because the coupling reaction between the hydrolysis product and the FR-ITR salt is much less affected by indoor or outdoor light than the corresponding coupling reaction between hydrolysis product and FVB salt.

As described in the foregoing, the present method employing the FR-ITR salt as coloring agent is an excellent method for assaying the enzyme activity, which has a number of important advantages.

In this specification and the attached claims, abbreviations are used as follows:

| Gly | Glycyl | $-HN-CH_2-CO-$ |
|---|---|---|
| Ala | Alanyl | $-HN-\underset{\underset{CH_3}{\mid}}{CH}-CO-$ |
| Val | Valyl | $-HN-\underset{\underset{CH(CH_3)_2}{\mid}}{CH}-CO-$ |
| Leu | Leucyl | $-NH-\underset{\underset{\underset{CH(CH_3)_2}{\mid}}{\underset{CH_2}{\mid}}}{CH}-CO-$ |

-continued

| | | |
|---|---|---|
| Ile | Isoleucyl | $\begin{array}{c}CH_3\\|\\CH_2\\|\\CH(CH_3)\\|\\-NH-CH-CO-\end{array}$ |
| Met | Methionyl | $\begin{array}{c}CH_3\\|\\S\\|\\(CH_2)_2\\|\\-NH-CH-CO-\end{array}$ |
| Pro | Prolyl | prolyl ring -CO- |
| Phe | Phenylalanyl | $\begin{array}{c}C_6H_5\\|\\CH_2\\|\\-NH-CH-CO-\end{array}$ |
| Gln | Glutaminyl | $\begin{array}{c}CONH_2\\|\\(CH_2)_2\\|\\-NH-CH-CO-\end{array}$ |
| Glu | Glutamyl | $\begin{array}{c}COOH\\|\\(CH_2)_2\\|\\-NH-CH-CO-\end{array}$ |
| pyroGlu | Pyroglutamyl | pyroglutamyl ring -CO- |
| Tyr | Tyrosyl | $\begin{array}{c}OH\\|\\C_6H_4\\|\\CH_2\\|\\-NH-CH-CO-\end{array}$ |
| Lys | Lysyl | $\begin{array}{c}NH_2\\|\\(CH_2)_4\\|\\-NH-CH-CO-\end{array}$ |
| Lys(Me) | α-N—methyl-lysyl | $\begin{array}{c}NH_2\\|\\(CH_2)_4\\|\\-N-CH-CO-\\|\\CH_3\end{array}$ |
| Arg | Arginyl | $\begin{array}{c}NH_2\\|\\C=NH\\|\\NH\\|\\(CH_2)_3\\|\\-NH-CH-CO-\end{array}$ |
| Ac | Acetyl | $CH_3CO-$ |

-continued

| | | |
|---|---|---|
| Bz | Benzoyl | $C_6H_5-CO-$ |
| Tos | p-Toluene-sulfonyl | $CH_3-C_6H_4-SO_2-$ |
| Boc | tert-Butoxy-carbonyl | $(CH_3)_3COCO-$ |
| Cbz | Benzyloxy-carbonyl | $C_6H_5-CH_2OCO-$ |
| Dansyl | Dansyl | 5-(dimethylamino)naphthalene-1-sulfonyl, $N(CH_3)_2$-naphthyl-$SO_2-$ |
| Glt | Glutaryl | $HOOC-(CH_2)_3-CO-$ |
| Me | Methyl | $CH_3-$ |
| NE | Naphthyl ester | $-O-$naphthyl |
| 6-Br—β-NE | 6-Bromo-β-naphthyl ester | $-O-$naphthyl$-Br$ |
| DMSO | Dimethyl sulfoxide | |

The method for assaying enzyme activity according to this invention is further illustrated below in detail with reference to Examples, wherein all amino acids are in L-form unless otherwise specifically indicated.

EXAMPLE 1

Influence of reaction temperature and reaction time upon the assay of kallikrein activity in urine using H-Pro-Phe-Arg-α-NE as substrate and FR-ITR salt or FVB salt as coloring agent:

To 1.0 ml of a 50 mM sodium phosphate buffer (pH 7.0) containing 0.015% of sodium dodecyl sulfate (SDS), were added 0.1 ml of urine and 0.1 ml of a 1.5 mM aqueous solution of H-Pro-Phe-Arg-α-NE. The mixture was incubated at 37° C. for 30 minutes. After addition of 0.1 ml of a 1-% aqueous FR-ITR salt solution or a 1-% aqueous FVB salt solution, the mixture was allowed to react under different temperature-time conditions of 0° C.-10 minutes, 25° C.-10 minutes, 25° C.-30 minutes, 37° C.-10 minutes, and 37° C.-30 minutes. Thereafter, each reaction mixture was admixed with 1.0 ml of glacial acetic acid and measured for the absorbance. The results obtained were as shown in Table 1.

TABLE 1

| Reaction conditions | | FVB salt | FR-ITR salt |
|---|---|---|---|
| Temp., °C. | Time, min. | Absorbance ($\lambda_{max}$, nm) | Absorbance ($\lambda_{max}$, nm) |
| 0 | 10 | 0.620 (500) | 0.620 (477) |
| 25 | 10 | 0.153 (510) | 0.628 (477) |
|  | 30 | 0.207 (510) | 0.625 (477) |
| 37 | 10 | 0.227 (513) | 0.625 (477) |
|  | 30 | 0.334 (513) | 0.621 (477) |

As is seen from the results shown in Table 1 when FVB salt is used, both the absorbance and $\lambda_{max}$ are affected by the reaction temperature and reaction time as if the concentration of kallikrein in urine had been varied, whereas when FR-ITR salt is used according to this invention, there is substantially no change in absorbance or in $\lambda_{max}$, both values remaining practically constant.

EXAMPLE 2

Figure 1:
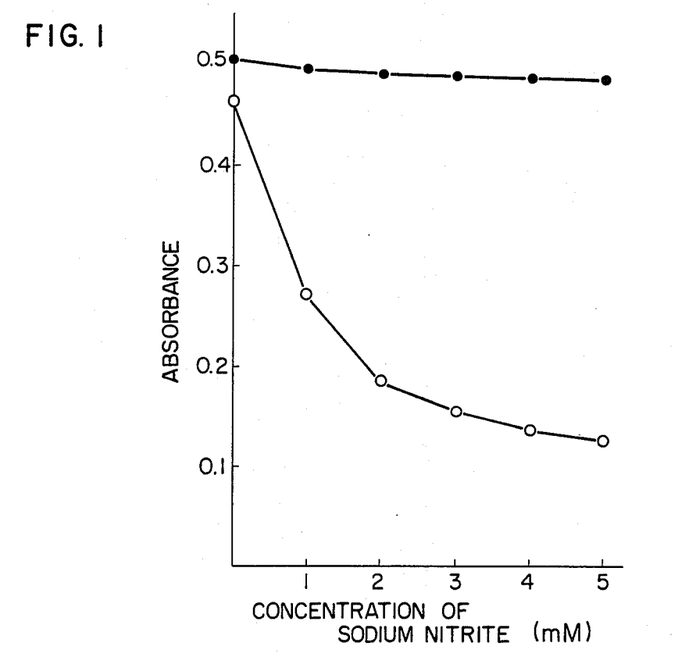
FIG. 1 shows the effect of nitrite ion upon the observed absorbance in the present method and the conventional method.

Influence of sodium nitrite upon the assay of kallikrein activity in urine using H-Pro-Phe-Arg-α-NE as substrate and FR-ITR salt or FVB salt as coloring agent:

To 1.0 ml of a 50 mM sodium phosphate buffer (pH 7.0) containing 0.015% of SDS, were added 0.1 ml of urine containing sodium nitrite in a concentration of 0, 1, 2, 3, 4, or 5 mM and 0.1 ml of a 1.5 mM aqueous H-Pro-Phe-Arg-α-NE solution. Each mixture was incubated at 37° C. for 30 minutes. In the case of using FR-ITR salt, 0.1 ml of a 1-% aqueous FR-ITR salt solution was added and the resulting mixture was allowed to react at 37° C. for 5 minutes. After addition of 1.0 ml of glacial acetic acid, the reaction mixture was measured for the absorbance at 475 nm. In the case of using FVB salt, 0.1 ml of a 1-% aqueous FVB salt solution was added and the mixture was allowed to react at 0° C. for 10 minutes. After addition of 1.0 ml of glacial acetic acid, the reaction mixture was measured for the absorbance at 505 nm. The results of measurements were as shown in FIG. 1, wherein the ordinate represents the absorbance and the abscissa the concentration of sodium nitrite; the coordinates marked with "●" represent the case of FR-ITR salt of this invention and those marked with "o" represent the case of FVB salt. It is seen from the above results that when FVB salt is used as the coloring agent, the absorbance is greatly affected by the presence of sodium nitrite as if the concentration of kallikrein in urine had been varied, whereas when FR-ITR salt is used according to this invention, the absorbance shows a practically constant value, without being substantially affected by the presence of sodium nitrite.

EXAMPLE 3

Figure 2:
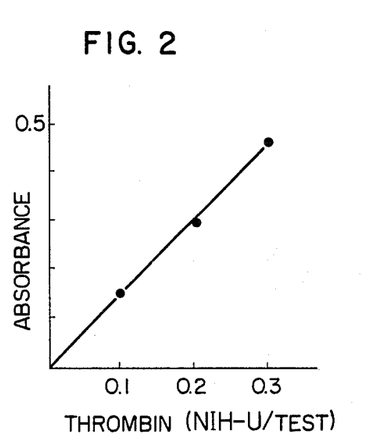
FIG. 2 shows the results of assay of thrombin by the present method.

Procedure for assaying thrombin by using Tos-Lys-α-NE:

To 1.7 ml of a 50-mM sodium phosphate buffer (pH 7.0), were added 0.1 ml of a thrombin solution (1, 2, or 3 NIH-U/ml) in physiological saline and 0.2 ml of a 1-mM aqueous Tos-Lys-α-NE solution. Each mixture was incubated at 25° C. for 10 minutes. After addition of 0.2 ml of a 1-% aqueous FR-ITR salt solution, the mixture was allowed to react at 25° C. for 5 minutes. The reaction mixture was admixed with 2.0 ml of 50-% acetic acid and measured for the absorbance at 475 nm. The results of the above measurements were as shown in FIG. 2, wherein the ordinate represents the absorbance and the abscissa the quantity of thrombin.

EXAMPLE 4

Figure 3:
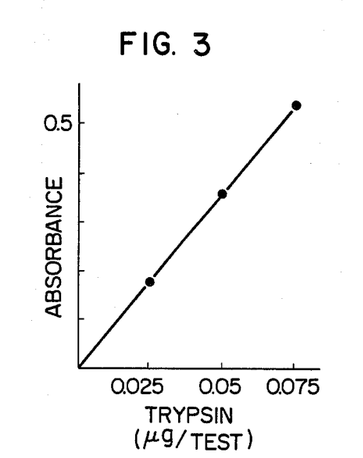
FIG. 3 shows the results of assay of trypsin by the present method.

Procedure for assaying trypsin by using Tos-Lys-α-NE:

To 1.7 ml of a 50-mM sodium phosphate buffer (pH 7.0), were added 0.1 ml of a trypsin solution (0.25, 0.5, or 0.75 μg/ml) in physiological saline and 0.2 ml of a 11mM aqueous Tos-Lys-α-NE solution. Each mixture was incubated at 25° C. for 15 minutes. After addition of 0.2 ml of a 1-% aqueous FR-ITR salt solution, the mixture was allowed to react at 25° C. for 5 minutes. The reaction mixture was then admixed with 2.0 ml of 50-% acetic acid and measured for the absorbance at 475 nm. The results of measurements were as shown in FIG. 3, wherein the ordinate represents the absorbance and the abscissa the quantity of trypsin.

EXAMPLE 5

Figure 4:
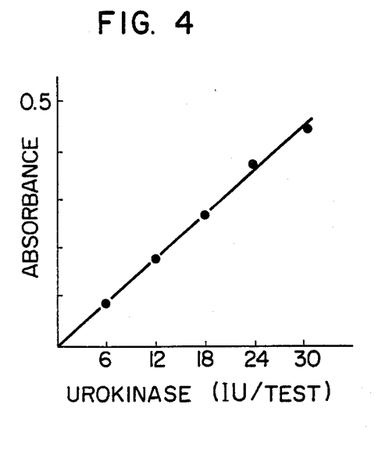
FIG. 4 shows the results of assay of urokinase by the present method.

Procedure for assaying urokinase by using Ac-Gly-Lys-α-NE:

To 1.7 ml of a 50-mM sodium phosphate buffer (pH 7.0), were added 0.1 ml of a urokinase solution (60, 120, 180, 240, or 300 IU/ml) in physiological saline and 0.2 ml of a 1-mM aqueous Ac-Gly-Lys-α-NE solution. Each mixture was incubated at 25° C. for 15 minutes. After additon of 0.2 ml of a 1-% aqueous FR-ITR salt solution, the mixture was allowed to react at 25° C. for 5 minutes. The reaction mixture was then admixed with 2.0 ml of 50-% acetic acid and measured for the absorbance at 475 nm. The results of measurements were as shown in FIG. 4, wherein the ordinate represents the absorbance and the abscissa the quantity of urokinase.

EXAMPLE 6

Figure 5:
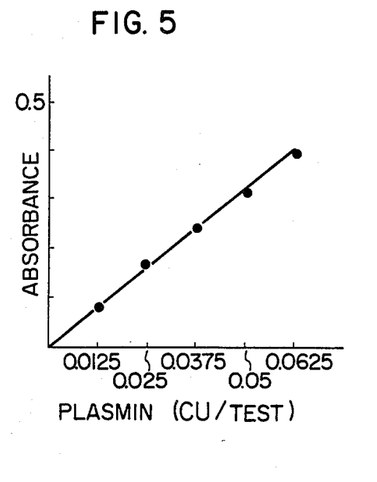
FIG. 5 shows the results of assay of plasmin by the present method.

Procedure for assaying plasmin by using H-D-Val-Leu-Lys-α-NE:

To 1.7 ml of a 50-mM sodium phosphate buffer (pH 7.0), were added 0.1 ml of a plasmin solution (0.125, 0.25, 0.375, 0.5, or 0.625 CU/ml) in physiological saline and 0.2 ml of a 10-% aqueous DMSO solution containing 1 mM of H-D-Val-Leu-Lys-α-NE. Each mixture was incubated at 25° C. for 15 minutes. After addition of 0.2 ml of a 1-% aqueous FR-ITR salt solution, the mixture was allowed to react at 25° C. for 5 minutes. The reaction mixture was then admixed with 2.0 ml of 50-% acetic acid and measured for the absorbance at 475 nm. The results of measurements were as shown in FIG. 5, wherein the ordinate represents the absorbance and the abscissa the quantity of plasmin.

EXAMPLE 7

Figure 6:
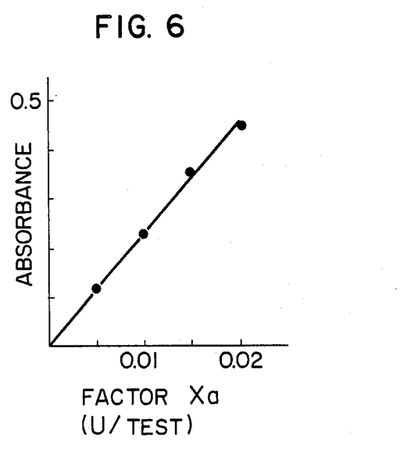
FIG. 6 shows the results of assay of Factor Xa by the present method.

Procedure for assaying Factor Xa by using Bz-Ile-Glu-Gly-Arg-α-NE:

To 1.7 ml of a 50-mM sodium phosphate buffer (pH 7.0), were added 0.1 ml of a Factor Xa solution (0.05, 0.1, 0.15, or 0.2 U/ml) in physiological saline and 0.2 ml of a 10-% aqueous DMSO solution containing 1 mM of Bz-Ile-Glu-Gly-Arg-α-NE. Each mixture was incubated at 20° C. for 15 minutes. After addition of 0.2 ml of a 1-% aqueous FR-ITR salt solution, the mixture was allowed to react at 20° C. for 5 minutes. The reaction mixture was then admixed with 2.0 ml of 50-% acetic acid and measured for the absorbance at 475 nm. The results of measurements were as shown in FIG. 6, wherein the ordinate represents the absorbance and the abscissa the quantity of Factor Xa.

EXAMPLE 8

Figure 7:
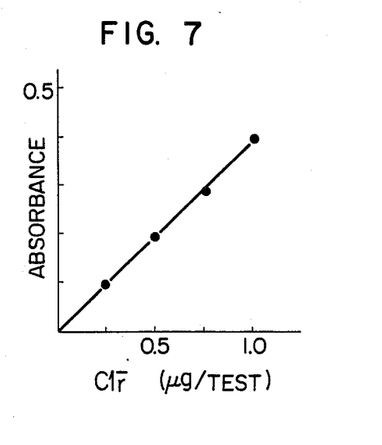
FIG. 7 shows the results of assay of $C\overline{1r}$ by the present method.

Procedure for assaying Clr̄ by using Ac-Gly-Lys-α-NE:

To 1.7 ml of a 50-mM sodium phosphate buffer (pH 7.0), were added 0.1 ml of a Clr̄ solution (2.5, 5, 7.5, or 10 μg/ml) in physiological saline and 0.2 ml of a -mM aqueous Ac-Gly-Lys-α-NE solution. The mixture was incubated at 25° C. for 15 minutes. After addition of 0.2 ml of a 1-% aqueous FR-ITR salt solution, the mixture was allowed to react at 25° C. for 5 minutes. The reaction mixture was then admixed with 2.0 ml of 50% acetic acid and measured for the absorbance at 475 nm. The results of measurements were as shown in FIG. 7, wherein the ordinate represents the absorbance and the abscissa the quantity of Clr̄.

EXAMPLE 9

Figure 8:
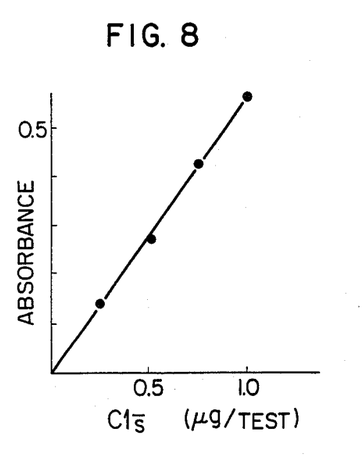
FIG. 8 shows the results of assay of $C\overline{1s}$ by the present method.

Procedure for assaying Cls̄ by using Ac-Tyr-α-NE:

To 1.7 ml of a 50-mM sodium phosphate buffer (pH 7.0), were added 0.1 ml of a Cls̄ solution (2.5, 5, 7.5, or 10 μg/ml) in physiological saline and 0.2 ml of a 10-% aqueous DMSO solution containing 1 mM of Ac-Tyr-α-NE. The mixture was incubated at 25° C. for 15 minutes. After addition of 0.2 ml of a 1-% aqueous FR-ITR salt solution, the mixture was allowed to react at 25° C. for 5 minutes. The reaction mixture was then admixed with 2.0 ml of 50-% acetic acid and measured for the absorbance at 475 nm. The results of measurements were as shown in FIG. 8, where the ordinate represents the absorbance and the abscissa the quantity of Cls̄.

EXAMPLE 10

Figure 9:
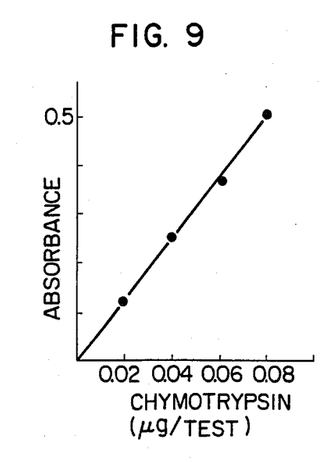
FIG. 9 shows the results of assay of chymotrypsin by the present method.

Procedure for assaying chymotrypsin by using Ac-Tyr-α-NE:

To 1.7 ml of a 50-mM sodium phosphate buffer (pH 7.0), were added 0.1 ml of a chymotrypsin solution (0.2, 0.4, 0.6, or 0.8 μg/ml) in physiological saline and 0.2 ml of a 10-% aqueous DMSO solution containing 1 mM of Ac-Tyr-α-NE. The mixture was incubated at 25° C. for 15 minutes. After addition of 0.2 ml of a 1-% aqueous FR-ITR salt solution, the mixture was allowed to react at 25° C. for 5 minutes. The reaction mixture was then admixed with 2.0 ml of 50-% acetic acid and measured for the absorbance at 475 nm. The results of measurements were as shown in FIG. 9, wherein the ordinate represents the absorbance and the abscissa the quantity of chymotrypsin.

EXAMPLE 11

Figure 10:
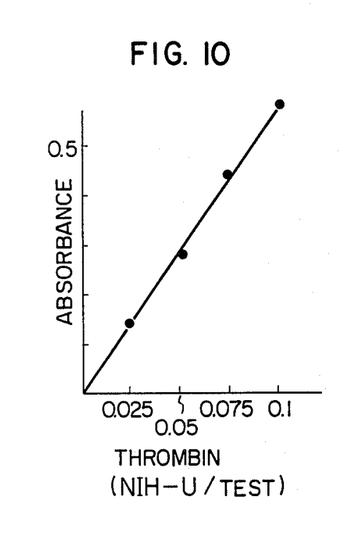
FIG. 10 shows the results of assay of thrombin by the present method.

Procedure for assaying thrombin by using Bz-Leu-Ala-Arg-α-NE:

To 1.7 ml of a 50-mM sodium phosphate buffer (pH 7.0), were added 0.1 ml of a thrombin solution (0.25, 0.5, 0.75, or 1.0 NIH-U/ml) in physiological saline and 0.2 ml of a 1-mM aqueous Bz-Leu-Ala-Arg-α-NE solution. The mixture was incubated at 25° C. for 15 minutes. After addition of 0.2 ml of a 1-% aqueous FR-ITR salt solution, the mixture was allowed to react at 25° C. for 5 minutes. The reaction mixture was then admixed with 2.0 ml of 50-% acetic acid and measured for the absorbance at 475 nm. The results of measurements were as shown in FIG. 10, wherein the ordinate represents the absorbance and the abscissa the quantity of thrombin.

EXAMPLE 12

Figure 11:
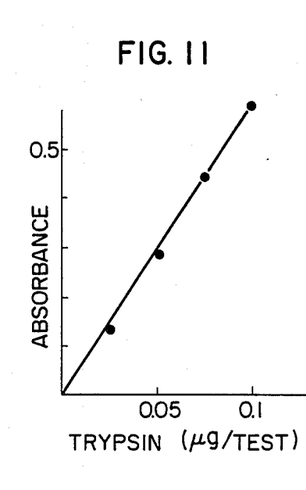
FIG. 11 shows the result of assay of trypsin by the present method.

Procedure for assaying trypsin by using Tos-Lys (Me)-β-NE:

To 1.7 ml of a 50-mM Tris-HCL buffer (pH 7.0), were added 0.1 ml of a trypsin solution (0.25, 0.5, 0.75, or 1.0 μg/ml) in physiological saline and 0.2 ml of a 1-mM aqueous Tos-Lys(Me)-β-NE solution. The mixture was incubated at 25° C. for 15 minutes. After addition of 0.2 ml of a 1-% aqueous FR-ITR salt solution, the mixture was allowed to react at 25° C. for 5 minutes. The reaction mixture was then admixed with 2.0 ml of glacial acetic acid and measured for the absorbance at 495 nm. The results of measurements were as shown in FIG. 11, wherein the ordinate represents the absorbance and the abscissa the quantity of trypsin.

EXAMPLE 13

Figure 12:
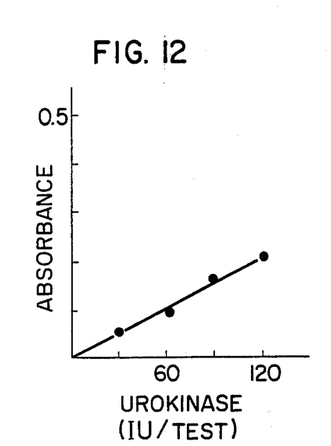
FIG. 12 shows the results of assay of urokinase by the present method.

Procedure for assaying urokinase by using Ac-Gly-Lys-6-Br-β-NE:

To 1.7 ml of a 50-mM sodium phosphate buffer (pH 7.0), were added 0.1 ml of a urokinase solution (300, 600, 900, or 1,200 IU/ml) in physiological saline and 0.2 ml of a 1-mM aqueous Ac-Gly-Lys-6-Br-β-NE solution. The mixture was incubated at 25° C. for 15 minutes. After addition of 0.2 ml of a 1-% FR-ITR salt solution, the mixture was allowed to react at 25° C. for 5 minutes. The reaction mixture was then admixed with 2.0 ml of glacial acetic acid and measured for the absorbance at 500 nm. The results of measurements were as shown in FIG. 12, wherein the ordinate represents the absorbance and the abscissa the quantity of urokinase.

EXAMPLE 14

Figure 13:
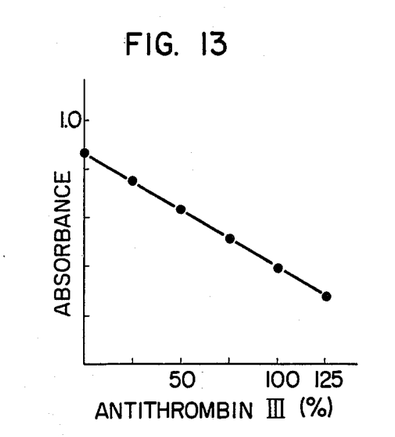
FIG. 13 shows the results of assay of antithrombin III by the present method.

Procedure for assaying antithrombin III by using Tos-Lys-α-NE:

To 1.0 ml of a 50-mM sodium phosphate buffer (pH 7.4) containing 1 IU/ml of heparin, were added 1.5 μl of a plasma containing antithrombin III in a concentration of 0, 25, 50, 75, 10, 100 or 125% of that in the normal plasma and 0.1 ml of a thrombin solution (1.5 NIH-U/ml) in physiological saline. To the mixture which had been incubated at 37° C. for 10 minutes, was added 0.1 ml of a 2-mM aqueous Tos-Lys-α-NE solution. The resulting mixture was further incubated at 37° C. for 10 minutes: After addition of 0.1 ml of a 1-% FR-ITR salt solution in 50-% acetic acid, the mixture was allowed to react at 37° C. for 5 minutes. The reaction mixture was then admixed with 1.0 ml of 50-% acetic acid and measured for the absorbance at 475 nm. The results of measurements were as shown in FIG. 13, wherein the ordinate represents the absorbance and the abscissa the quantity of antithrombin III.

EXAMPLE 15

Figure 14:
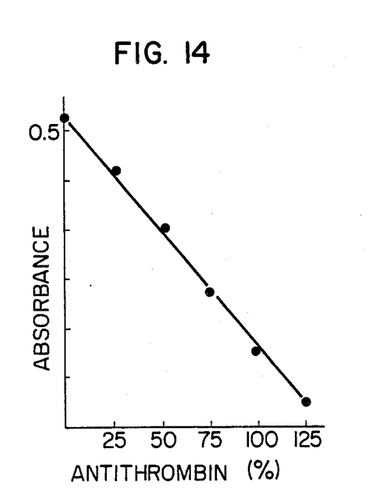
FIG. 14 shows the results of assay of antithrombin III by the present method.

Procedure for assaying antithrombin III by autoanalyzer using Tos-Lys-α-NE:

To 20 μl of a plasma containing antithrombin III in a concentration of 0, 25, 50, 75, 100, or 125% of that in the normal plasma, were added 1.0 ml of a 50-mM sodium phosphate buffer (pH 7.4) containing thrombin (4 U/ml), heparin (5 U/ml), and bovine serum albumin (1 mg/ml). The mixture, which had been incubated at 37° C. for 2 minutes, was admixed with 0.1 ml of a 2-mM aqueous Tos-Lys-α-NE solution containing 1% of FR-ITR salt and further incubated at 37° C. for 30 seconds. The reaction mixture was admixed with 1.0 ml of 50-% acetic acid and, one minute thereafter, was measured for the absorbance at 540 nm. The autoanalyzer employed was "Cobas-Bio" (Kabi Co.). The results of measurements were as shown in FIG. 14, wherein the ordinate represents the absorbance and the abscissa the quantity of antithrombin III.

EXAMPLE 16

Figure 15:
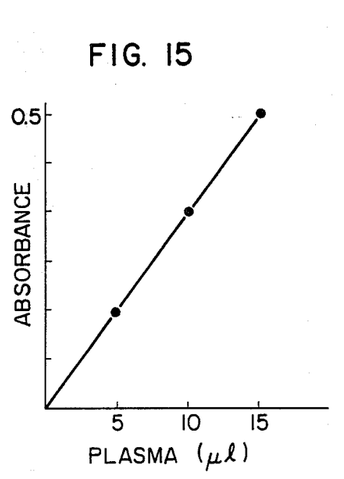
FIG. 15 shows the results of assay of plasma prekallikrein by the present method.

Procedure for assaying plasma prekallikrein by using H-pro-Phe-Arg-α-NE:

To 2.0 ml of a 50-mM sodium phosphate buffer (pH 6.0), were added a citrated plasma (5, 10, or 15 μl) and 10 μl of an aqueous dextran sulfate (molecular weight 500,000) solution (30 μg/ml). The mixture, which had been incubated at 37° C. for 5 minutes, was admixed with 0.2 ml of a 2-mM aqueous H-Pro-Phe-Arg-α-NE solution containing 0.1% SDS and again incubated at 37° C. for 10 minutes. After addition of 0.2 ml of 50-% acetic acid containing 1% of FR-ITR salt, the mixture was allowed to react at 37° C. for 5 minutes. The reaction mixture was then admixed with 2.0 ml of 50-% acetic acid and measured for the absorbance at 475 nm. The results of measurements were as shown in FIG. 15, wherein the ordinate represents the absorbance and the abscissa the quantity of plasma.

EXAMPLE 17

Figure 16:
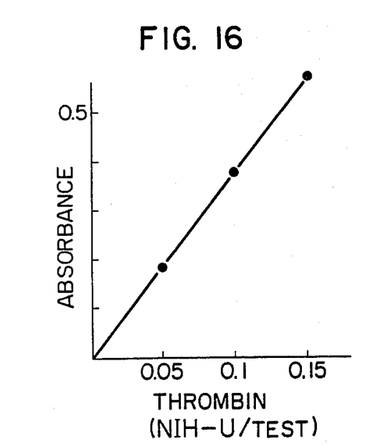
FIG. 16 shows the results of assay of thrombin by the present method.

Procedure for assaying thrombin by use of Tos-Lys-α-NE:

To 1.7 ml of a 50-mM sodium phosphate buffer (pH 8.0), were added 0.1 ml of a thrombin solution (0.5, 1, or 1.5 NIH-U/ml) in physiological saline and 0.2 ml of a 1.5-mM aqueous Tos-Lys-α-NE solution. The mixture was incubated at 37° C. for 10 minutes, then admixed with 0.2 ml of a 1-% FR-ITR salt solution in 50-% acetic acid, and allowed to react at 37° C. for 5 minutes. After addition of 2.0 ml of 50-% acetic acid, the reaction mixture was measured for the absorbance at 475 nm. The results of measurements were as shown in FIG. 16, wherein the ordinate represents the absorbance and the abscissa the quantity of thrombin.

EXAMPLE 18

Figure 17:
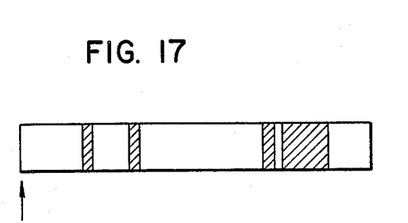
FIG. 17 shows an enzyme pattern in the blood as determined by the present method; the mark " ↑ " indicates the origin.

Electrophoretic determination of the enzyme pattern in blood:

A polyacrylamide gel column was prepared using a glass tube of 4 mm in internal diameter and 7 cm in length. The column was loaded with 40 μl of a serum and subjected to electrophoresis at 2 mA for about 50 minutes. The gel was taken out of the tube, then immersed in 10 ml of a solution of 0.5 mM of Tos-Lys-α-NE in a 100-mM sodium phosphate buffer (pH 7.0), and incubated at 25° C. for 30 minutes. After addition of 1 ml of a 1-% aqueous FR-ITR salt solution, the gel was left standing at 25° C. for 10 minutes to effect staining. It was thus possible to observe the enzyme pattern in blood in the form of orange red bands. In FIG. 17 are shown the results obtained by using a normal human serum.

EXAMPLE 19

Procedure for staining of blood cells:

A blood smear was prepared and fixed with formalin vapor. After washing with water, the specimen was immersed in 10 ml of a 100-mM sodium phosphate buffer (pH 7.0) containing 0.2 mM of a substrate (Ac-Tyr-α-NE, Tos-Lys-α-NE, or Ac-Gly-Lys-α-NE) and 0.1% of FR-ITR salt, and incubated at 25° C. for 90 minutes. The specimen was washed with water and observed under a microscope. The results of staining were as shown in Table 2.

TABLE 2

|  | Ac—Tyr—α-NE | Tos—Lys—α-NE | Ac—Gly—Lys—α-NE |
|---|---|---|---|
| Lymphocyte | − | − | − |
| Monocyte | ±~+ | ±~+ | + |
| Granulocyte |  |  |  |
| Neutrophil | +++ | +++. | +++ |
| Eosinophil | − | − | − |
| Basophil | + | + | + |

Note:
−: Non-staining;
± to +++: Degree of staining

EXAMPLE 20

Sensitivities to various enzymes, as assayed by the procedures of Examples 1 to 17, were as shown in Table 3.

TABLE 3

| Substrate | Enzyme | Sensitivity | Unit |
|---|---|---|---|
| H—pyroGlu—Gly—Arg—α-NE | Thrombin | 0.197 | ΔO,D/NIH-U/min |
| H—Leu—Gly—Arg—α-NE | Thrombin | 0.261 | ΔO,D/NIH-U/min |
| H—D—Val—Leu—Arg—α-NE | Kallikrein | 1.387 | ΔO,D/KU/min |
| Bz—Phe—Val—Arg—α-NE | Thrombin | 0.053 | ΔO,D/NIH-U/min |
| Tos—Gly—Pro—Arg—α-NE | Kallikrein | 1.747 | ΔO,D/KU/min |
| H—Phe—Val—Arg—α-NE | Thrombin | 0.173 | ΔO,D/NIH-U/min |
| Glt—Gly—Arg—α-NE | Thrombin | 0.115 | ΔO,D/NIH-U/min |
| H—Gly—Gly—Arg—α-NE | Thrombin | 0.377 | ΔO,D/NIH-U/min |
| H—Phe—Arg—α-NE | Kallikrein | 1.420 | ΔO,D/KU/min |
| Tos—Gly—Pro—Lys—α-NE | Urokinase | $3.55 \times 10^{-4}$ | ΔO,D/IU/min |
| Ac—Met—α-NE | Kallikrein | 0.0347 | ΔO,D/KU/min |

EXAMPLE 21

Figure 18:
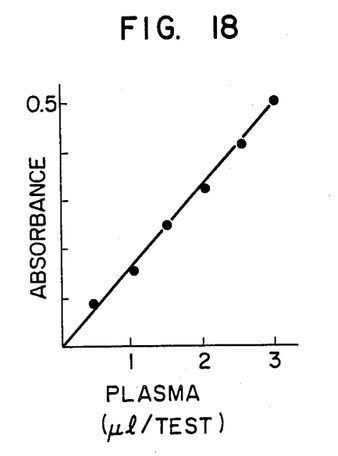
FIG. 18 shows the results of assay of plasminogen by the present method.

Procedure for assaying plasminogen by using Tos-Lys-α-NE:

To 1.0 ml of a human plasma solution (3, 2.5, 2, 1.5, 1, or 0.5 μl plasma/50 mM sodium phosphate buffer), was added 0.1 ml of an aqueous streptokinase solution (1,000 U/ml). The mixture was incubated at 37° C. for 10 minutes, then admixed with 0.1 ml of a 2-mM Tos-Lys-α-NE solution, and again incubated at 37° C. for 10 minutes. To the mixture, was added 0.1 ml of a 1-% FR-ITR salt solution in 50-% acetic acid. The mixture was allowed to react at 37° C. for 10 minutes. After addition of 1.0 ml of glacial acetic acid, the reaction mixture was measured for the absorbance at 475 nm. The results of measurements were as shown in FIG. 18, wherein the ordinate represents the absorbance and the abscissa the quantity of plasma.

EXAMPLE 22

Figure 19:
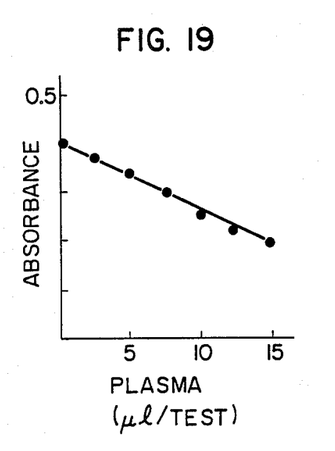
FIG. 19 shows the results of assay of antiplasmin by the present method.

Procedure for assaying antiplasmin by using Tos-Lys-α-NE:

To 1.0 ml of a human plasma solution (15, 12.5, 10, 7.5, 5, or 2.5 µl plasma/50 mM sodium phosphate buffer (pH 7.4)), was added 0.1 ml of an aqueous plasmin solution (0.1 CU/ml). The mixture was incubated at 37° C. for 20 seconds, then admixed with 0.1 ml of a 2 mM Tos-Lys-α-NE solution, and again incubated at 37° C. for 10 minutes. To the mixture, was added 0.1 ml of a 1-% FR-ITR salt solution in 50-% acetic acid. The mixture was allowed to react at 37° C. for 10 minutes. After addition of 1.0 ml of glacial acetic acid, the reaction mixture was measured for the absorbance at 475 nm. The results of measurements were as shown in FIG. 19, wherein the ordinate represents the absorbance and the abscissa the quantity of plasma.

EXAMPLE 23

Figure 20:
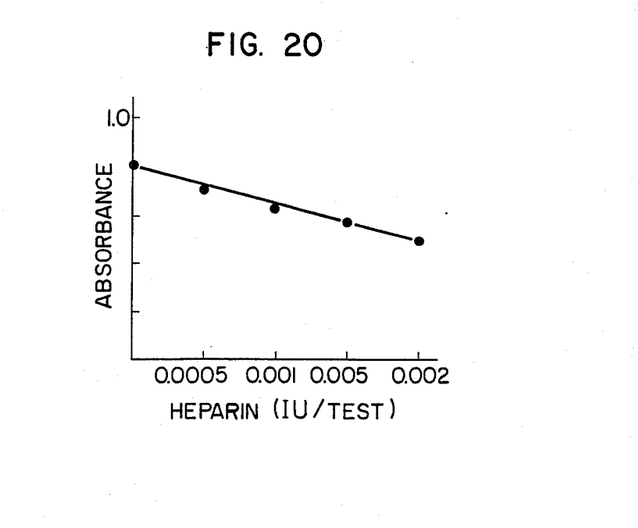
FIG. 20 shows the results of assay of heparin by the present method.

Procedure for assaying heparin by using Tos-Lys-α-NE:

To 0.05 ml of an aqueous solution containing 0.01, 0.02, 0.03, or 0.04 IU/ml of heparin, were added 0.05 ml of a standard plasma diluted tenfold with physiological saline, 1.0 ml of a 50-mM sodium phosphate buffer, and 0.1 ml of an aqueous thrombin solution (1.5 NIH-U/ml). To the mixture, after incubation at 37° C. for 10 minutes, was added 0.1 ml of a 2-mM Tos-Lys-α-NE solution. The resulting mixture was again incubated at 37° C. for 10 minutes. After addition of 0.1 ml of a 1-% FR-ITR salt solution in 50-% acetic acid, the mixture was allowed to react at 37° C. for 10 minutes, then admixed with 1.0 ml of glacial acetic acid, and measured for the absorbance at 475 nm. The results of measurements were as shown in FIG. 20, wherein the ordinate represents the absorbance and the abscissa the quantity of heparin.

EXAMPLE 24

Figure 21:
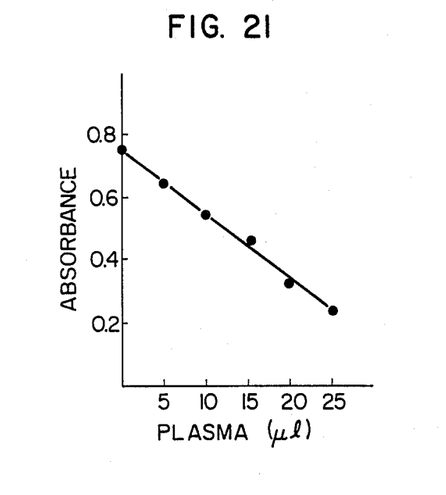
FIG. 21 shows the results of assay of anti-thrombin III by the present method.

Procedure for assaying antithrombin III by use of Tos-Lys-α-NE:

To 0, 5, 10, 15, 20, or 25 µl of a plasma, was added 3.0 ml of a 50-mM sodium phosphate buffer (pH 7.4) containing 0.8 NIH-U/ml of thrombin, 4 IU/ml of heparin, and 10 KIE/ml of aprotinin. A 50 µl portion of the mixture was placed in a test tube and incubated at 37° C. for 10 minutes. To the mixture, was added 0.1 ml of a 2-mM Tos-Lys-NE solution. The resulting mixture was again incubated at 37° C. for 10 minutes. After addition of 0.1 ml of a 1-% FR-ITR salt solution in 10-% acetic acid, the mixture was allowed to react at 37° C. for 10 minutes, then admixed with 2.0 ml of 30-% acetic acid, and measured for the absorbance at 475 nm. The results of measurements were as shown in FIG. 21, wherein the ordinate represents the absorbance and the abscissa the quantity of plasma.

EXAMPLE 25

Figure 22:
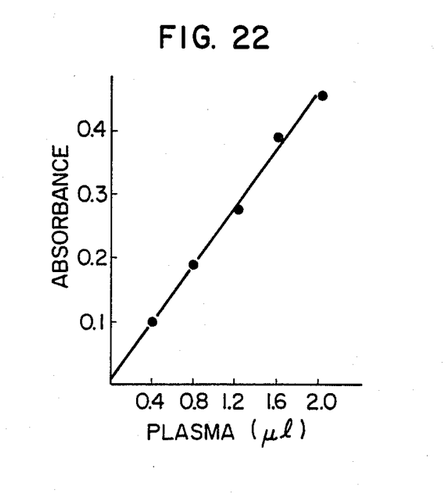
FIG. 22 shows the results of assay of prothrombin by the present method.

Procedure for assaying prothrombin by use of Tos-Lys-α-NE:

To 1.0 ml of a human plasma solution (2.0, 1.6, 1.2, 0.8, or 0.4 µl plasma/50 mM sodium phosphate buffer), was added 0.1 ml of a solution of a snake venom (*Echis carinatus* venom; 10 µg/ml) in the buffer. The resulting mixture was incubated at 37° C. for 5 minutes, then admixed with 0.1 ml of a 2 mM Tos-Lys-α-NE solution, and again incubated at 25° C. for 30 minutes. After addition of 0.1 ml of a 1-% FR-ITR salt solution in 50-% acetic acid, the mixture was allowed to react at 37° C. for 10 minutes. The reaction mixture was admixed with 1.0 ml of glacial acetic acid and measured for the absorbance at 475 nm. The results of measurements were as shown in FIG. 22, wherein the ordinate represents the absorbance and the abscissa the quantity of plasma.

What is claimed is:

1. A method of assaying an enzyme, which comprises allowing the enzyme to react with a substrate of the formula

1. A method of assaying an enzyme, which comprises allowing the enzyme to react with a substrate of the formula (I)

wherein $R_1$ represents an amino acid or an oligopeptide combined in the form of ester through the C-terminal carboxyl group of said amino acid or oligopeptide and $R_2$ represents a hydrogen or bromine atom to hydrolyze the substrate, then allowing the hydrolysis product of the formula.

to react with a FR-ITR salt to form a pigment, and determining the pigment.

2. A method according to claim 1, wherein $R_1$ is A-$R_3$-$R_4$-$R_5$-$R_6$-CO-, in which A represents a hydrogen atom or an acyl or sulfonyl group, $R_3$, $R_4$ and $R_5$ each represent Gly, Ala, Val, Leu, Ile, Pro, Phe, Gln, Glu pyroGlu or a single bond, and $R_6$ represents Lys, Lys(Me), Arg, Met or Tyr.

3. A method according to claim 2, wherein A is a hydrogen atom or Ac, Bz, Tos, Boc, Cbz, Dansyl or Glt.

4. A method according to claim 3, wherein $R_1$ is A-Tyr-, A-Arg-, A-Lys-, A-Gly-Lys-, A-Phe-Arg-, A-Gly-Gly-Arg-, A-Leu-Gly-Arg-, A-Gln-Gly-Arg-, A-pyroGlu-Gly-Arg-, A-Leu-Ala-Arg-, A-Pro-Phe-Arg-, A-D-Val-Leu-Lys-, A-Phe-Val-Arg- or A-Ile-Glu-Gly-Arg-.

5. A method according to any of claims 1 to 4, wherein the formula (I) is Tos-Lys-α-NE, Ac-Tyr-α-NE, Bz-Leu-Ala-Arg-α-NE, Ac-Phe-Arg-α-NE, H-Pro-Phe-Arg-α-NE or Ac-Gly-Lys-α-NE.

6. A method according to any of claims 1 to 4, wherein the enzyme is serine protease of E.C. 3.4.21.

7. A method according to any of claims 1 to 4, wherein the enzyme is trypsin, chymotrypsin, kallikrein, plasmin, thrombin, urokinase, factor Xa, $\overline{Cls}$ or $\overline{Clr}$.

8. A method according to claim 5, wherein the enzyme is serine protease of E.C. 3.4.21.

9. A method according to claim 5, wherein the enzyme is trypsin, chymotrypsin, kallikrein, plasmin, thrombin, urokinase, factor Xa, $\overline{Cls}$ or $\overline{Clr}$.

10. A method according to any of claims 1 to 4, wherein the enzyme is an unreacted enzyme which remains after reaction of the enzyme with an inhibitor.

11. A method according to any of claims 1 to 4, wherein the enzyme is an unreacted enzyme which remains after reaction of the enzyme with an inhibitor which is antithrombin III, heparin or antiplasmin.

12. A method according to any of claims 1 to 4, wherein the enzyme is an enzyme which is obtained by a reaction of a zymogen with an activator for the zymogen.

13. A method according to any of claims 1 to 4, wherein the enzyme is an enzyme which is obtained by the reaction of a zymogen with an activator for the zymogen, said zymogen being prekallikrein or plasminogen.

14. A method of assaying an enzyme, which comprises allowing the enzyme to react with a substrate of the formula (I)

wherein $R_1$ represents an amino acid or an oligopeptide combined in the form of ester through the C-terminal carboxyl group of said amino acid or oligopeptide and $R_2$ represents a hydrogen or bromine atom at 20° to 40° C. for 2 hours or less to hydrolyze the substrate, then allowing the hydrolysis product of the formula to react with a FR-ITR salt at 20° to 40° C. for 2 hours or less to form a pigment, and determining the pigment.

15. A method according to claim 14, wherein each reaction is carried out at the same temperature.

16. A method according to claim 14, wherein hydrolysis is carried out at 20° to 37° C. for 30 seconds to 90 minutes and reaction of the FR-ITR salt is carried out at 25° to 40° C. for 30 seconds to 90 minutes.

17. A method according to claim 16, wherein each reaction is carried out at the same temperature.

18. A method of assaying an enzyme, which comprises allowing the enzyme to react in the presence of nitrite ion with a substrate of the formula (I)

wherein $R_1$ represents an amino acid or an oligopeptide combined in the form of ester through the C-terminal carboxyl group of said amino acid or oligopeptide and $R_2$ represents a hydrogen or bromine atom to hydrolyze the substrate, then allowing the hydrolysis product of the formula to react with a FR-ITR salt to form a pigment, and determining the pigment.

19. A method according to claim 18 wherein said enzyme is reacted with the substrate in the presence of urine containing nitrite ion.

20. A method of assaying an enzyme, which comprises allowing the enzyme to react with a subsrate of the formula .

(I)

wherein $R_1$ represents an amino acid or an oligopeptide combined in the form of ester through the C-terminal carboxyl group of said amino acid or oligopeptide and $R_2$ represents a hydrogen or bromine atom to hydrolyze the substrate, terminating the reaction between enzyme and substrate by acidification;

then allowing the hydrolysis product of the formula to react with a FR-ITR salt under acidic conditions to form a pigment, and determining the pigment.

21. A method of assaying an enzyme, which comprises allowing the enzyme to react with a substrate of the formula (I)

wherein $R_1$ represents an amino acid or an oligopeptide combined in the form of ester through the C-terminal carboxyl group of said amino acid or oligopeptide and $R_2$ represents a hydrogen or bromine atom at 20° to 40° C. for 2 hours or less to hydrolyze the substrate, then allowing the hydrolysis product of the formula to react with a FR-ITR salt at 20° to 40° C. for 2 hours or less and at a pH of 1 to 4 to form a pigment, and determining the pigment.

* * * * *